United States Patent [19]

Martin

[11] Patent Number: 4,654,374

[45] Date of Patent: * Mar. 31, 1987

[54] CHEMICAL DISINFECTANT AND STERILANT

[76] Inventor: Howard Martin, 909 Pershing Dr., Silver Spring, Md. 20910

[ * ] Notice: The portion of the term of this patent subsequent to Sep. 4, 2001 has been disclaimed.

[21] Appl. No.: 709,908

[22] Filed: Mar. 8, 1985

[51] Int. Cl.$^4$ ............... A01N 31/08; A01N 35/00; A01N 43/64; C11D 3/48
[52] U.S. Cl. ................................ 514/698; 252/106; 514/359; 514/705; 514/731; 514/736
[58] Field of Search ............... 514/698, 705, 736, 731, 514/359; 252/106

[56] References Cited

U.S. PATENT DOCUMENTS

| | | | |
|---|---|---|---|
| 3,915,877 | 10/1975 | Ware | 252/106 |
| 4,208,404 | 6/1980 | Cowan | 424/153 |
| 4,469,614 | 9/1984 | Martin | 514/705 |

Primary Examiner—Allen J. Robinson
Attorney, Agent, or Firm—Walter G. Finch

[57] ABSTRACT

The invention is an improved disinfectant and sterilant in a chemical form. The disinfectant and sterilant formulation is based upon glutaraldehyde which must be in acidic form. The normal pH range for the disinfectant and sterilant is 3.0–3.5, however, under controlled circumstances the range may be 2.5–7.0; as the disinfectant and sterilant must be acidic, it cannot be over pH 7.0. In use as a disinfectant by immersion, the items or materials remain immersed for up to ten minutes. As a sterilant, the immersion is between six and ten hours. The disinfectant and sterilant consists of a plurality of chemicals mixed with the glutaraldehyde as a solution.

7 Claims, No Drawings

CHEMICAL DISINFECTANT AND STERILANT

BACKGROUND AND SUMMARY OF THE INVENTION

This invention is an improvement over the chemical disinfectant and sterilant composition disclosed in my U.S. Pat. No. 4,469,614 issued Sept. 4, 1984.

The invention relates to antiseptic and germicidal compositions and in particular to disinfectants and sterilants. Specifically, it relates to chemical compositions for use as disinfectants and sterilants.

There have been many compositions developed for antiseptic and germicidal cleansing purposes, but each in the prior art has had some limitations as to the applications. For some the limitation has been the extent to which they could successfully disinfect. For others the limitation has been the extent to which they could consistently sterilize. Still others were limited because of the toxic effect on the skin or other organs of the user. Other compositions were limited because of their corroding effect on metal, such as spotting or tarnishing.

The present invention has been developed to avoid or overcome these prior art limitations especially in the general use solutions of the disinfectant and sterilant. This is particularly so when used as a disinfectant and sterilant for inanimate objects.

The present invention has many uses for disinfecting or sterilizing hard surfaces, such as counter tops, laboratory tables, laboratory equipment, hospital walls, and other such hard surface items or areas in medical, surgical or dental environments.

The disinfectant and sterilant of the present invention is specifically intended as a means of fighting organisms that cause disease. The disinfectant and sterilant may be used in laboratories, operating rooms, patient-care rooms or areas, and other similar places in public or private facilities such as schools, hospitals, homes, factories, and similar locations.

The disinfectant and sterilant is intended for use to eliminate bacteria that is found on hard surfaces as aforementioned. The use of the present invention may be for application by spraying, wiping, rinsing, dipping, brushing, or by other methods of application.

The basic ingredients of the formula for the disinfectant and sterilant composition, which is delineated in detail hereinafter, is composed of glutaraldehyde, ortho phenyl phenol, paratertiaryamylphenol, benzotriazole, sodium arylalkylsulfonate, and citric acid. The plurality of chemicals is mixed as a solution.

The disinfectant and sterilant is provided as a stock solution, thereafter, in activated form, it is diluted with water in various proportions or ratios depending upon the level necessary to achieve a specified end result. This is discussed in detail hereinafter.

Of particular note is the fact that in the prior art the use of glutaraldehyde has usually been in the alkaline form, whereas in the present invention the use of glutaraldehyde is in the acid form.

The prior art disinfectants in the alkaline solutions tend to leave a residue in the more concentrated forms. This could be an irritant. Several rinses may be required to remove the slippery residue.

The present invention is primarily for use as a disinfectant and sterilant on inanimate surfaces for disinfection and sterilization of contaminated areas. For example, on dental or surgical instruments that are contaminated.

As a secondary use, the present invention may be used in a milder form, by dilution, as a hand disinfectant in health case offices, laboratories, and treatment rooms.

The normal pH range for the disinfectant and sterilant of this invention is 3.0–3.5, however, under controlled circumstances the range may be 2.5–7.0; as the disinfectant and sterilant must be acidic, it cannot be over pH 7.0.

When aused as a disinfectant by immersion, the items or materials remain immersed for up to ten minutes. As a sterilant, the immersion is between six and ten hours.

As noted, the present invention uses the glutaraldehydes in the acidic form. In the prior art the glutaraldehydes in the alkaline form present certain disadvantages. Some of these disadvantages are: it needs an activator of a special solution or powder to make it active; once activated, it then has a limited life of one to four weeks and must be disposed of entirely; the composition, which is normally activated in approximate amounts of a liter, is uneconomical if not used because it is dated at time of activation and must be discarded; the solution yellows the skin due to a tanning action; it has a disagreeable odor; and it is corrosive.

In the present invention, the acid form of the glutaraldehyde needs no activation and has a more or less indefinite shelf life of close to one year. The solution of the present invention permits mixing and diluting just the amount needed, thereby preserving the stock solution which makes it more economical. In this manner it does not need dating, for the mixture being used is only what is needed.

In the prior art the corrosion of instruments (when used for dental and surgical instrument disinfection or sterilization), the tanning effect on the skin, irritation of the skin and allergic dermatitis to the skin, its noxious odor, general toxicity, and the tarnishing of carbon steel instruments were all undesirable problems. The present invention overcomes these problems.

Use of the present invention is less irritating, because of the lower concentration in the useable dilutions. For example, in a 1:10 dilution there is no effect on the skin in a ten minute immersion. At the same time, a one percent concentration of glutaraldehyde in the acidic form will kill bacteria if contact is made.

The present invention has a much wider and universal use than the disinfectants and sterilants of the prior art which were limited because of the prior art problems. The present invention may be used on and for all hard surfaces that are non-porous. Hard surface items include catheters, scalpels, trays, bowls, dental mirrors, lights, and other similar equipment. Even cotton swabs may be soaked in it and then used to disinfect.

In general use the present invention may be used for instrument immersion, wiping surfaces and instruments, dipping, and spraying (by pump or aerosol means).

The present invention may also be used by placing instruments in a tray containing the disinfectants and sterilant in diluted solution form. This includes all medical and other health care arrangements, including veterinary, podiatry, hospital, nursing, and other health care facilities or laboratories. Cages for laboratory animals and the laboratory areas may be disinfected with the present invention. In household use the present invention may be used where ordinary sprays are used, such as in toilet bowls, animal areas, and kitchen areas. The present invention is effective on items that cannot be heated or autoclaved, and includes rubber and plastics items.

In one of the milder forms, by diluting on a 1:80 basis (or in higher concentrations where permissible) the present invention may be used in soaps for degerming the hands or as a presurgical lotion as a hand degerming agent.

It is, therefore, an object of this invention to provide a disinfectant and sterilant that is a chemical composition.

It is another object of this invention to provide a disinfectant and sterilant that may be used on hard surface inanimate objects.

It is also an object of this invention to provide a disinfectant and sterilant that may be used on living tissue.

It is yet another object of this invention to provide a disinfectant and sterilant that fights organisms that cause disease.

It is still another object of this invention to provide a disinfectant and sterilant that uses glutaraldehyde in acid form.

Further objects and advantages of the invention will become more apparent in light of the following description of the preferred embodiments.

DESCRIPTION OF THE PREFERRED EMBODIMENTS

The formula of the present invention for a chemical disinfectant and sterilant is as follows:

| | |
|---|---|
| glutaraldehyde (acidic) | 15.46% |
| orthophenyl phenol | 0.34% |
| paratertiaryamylphenol | 0.07% |
| benzotriazole | 0.24% |
| sodium arylalkylsulfonate | 3.40% |
| citric acid | 0.34% |
| water | 80.15% |
| TOTAL (By Weight) | 100.00% |

The above formulation is the base stock solution and when used, as hereinafter described, it is diluted. The base stock solution is the concentrated form and it is further diluted with water for clinical or general use. The percentages are by weight of the ingredients to the total weight of the mixture.

It is to be noted that the aforementioned stock solution is shown as a liquid solution, however, it is to be understood that the reduction or transformation to a dry powder state as a dry base stock chemical compound, for subsequent dissolving in water or other suitable solvent to form the base stock solution, is within the scope and intent of this invention.

It is also to be understood that the mixing of the formula without the water content as a liquid base stock chemical compound, for subsequent addition of the water content to form the base stock solution, is also within the scope and intent of this invention.

The formulation of the aforementioned chemical disinfectant and sterilant in a dry base stock chemical compound and in a liquid base stock chemical compound are means by which economical storage and shipment can be obtained in relation to the aforementioned base stock solution which is of greater volume.

The glutaraldehyde in the formula is in acid form with a preferred pH range of 3.0–3.5. However, a pH range of 2.5–7.0 is possible and useable under controlled conditions. The glutaraldehyde for this invention must be acidic and, therefore, must not exceed a pH of 7.0, in that regard the range slightly below the pH of 7.0 is desirable.

The glutaraldehyde and the sodium biphosphate are each a 10.0% concentration chemical compound, mixed into the formulation in weights, or percentages of the total weight, as noted hereinbefore. The formulation given previously by percentages of the total weight for each ingredient, are shown below by actual weight of each ingredient for the formulation:

| Ingredient | Weight (grams) | Percent of Total Wgt. |
|---|---|---|
| glutaraladehyde (acidic) | 227.20 | 15.46 |
| orthophenyl phenol | 5.00 | 0.34 |
| paratertiaryamylphenol | 1.00 | 0.07 |
| benzotriazole | 3.50 | 0.24 |
| sodium arylalkylsulfonate | 50.00 | 3.40 |
| citric acid | 5.00 | 0.34 |
| water | 1177.60 | 80.15 |
| TOTAL | 1469.30 | 100.00 |

The citric acid removes a noxious odor and provides additional acidification.

To activate the chemical disinfectant and sterilant for use, the base stock solution is diluted in controlled ratios with water. The normal range of activated solutions is generally from a ratio of 1:10 to 1:80; that is one part base stock solution to nine parts water for a strong solution, and one part base stock solution to seventy-nine parts water for a weak solution. These are for disinfecting purposes. For sterilization the range is 1:5 to 1:10, depending upon the severity of the need.

The range of activated solutions from the ratio of 1:10 to the ratio of 1:80 are for selected uses for disinfecting. The determination of the ratio to use may be determined by test for the wide plurality of applications which exist. For example, the disinfection of kidney dialysis applications must be a ratio of 1:35, while for general hospital or office disinfection it may be a ratio of 1:20.

The benzotriazole and sodium arylalkylsulfonate act as surfactants and corrosion inhibitors. Sodium silicate (3.0%) or sodium nitrate (10 grams per liter) may be substituted for the benzotriazole and such a substitution is within the scope and intent of the present invention.

The weights for each ingredient, and their corresponding percentages of the total weight of the mixture, are for the optimal formula and preferred embodiment of the invention of a chemical disinfectant and sterilant. However, it is to be understood that variations from this optimal formula of up to plus or minus ten percent of each weight are workable and are within the scope and intent of this invention, any difference in total weight being adjusted in the water content; the percentages by weight being adjusted accordingly. Thus, the formula has a range of weight for each ingredient with the optimal and preferred embodiment being as specifically listed.

In the use of the base stock solution of the chemical disinfectant and sterilant in the diluted state, solutions weaker than the 1:80 ratio begin to lose their effectiveness or the ability to meet some desired level of disinfection. While such weaker solutions may be used, they are not recommended for best results. Whenever the solution being used is at such a weaker ratio it may be desirable to perform tests in order to assure the desired results are being obtained. For that reason such weaker ratios are not recommended.

In using the present invention for disinfection by immersion, ultrasonic activation of the mass will speed up the process of disinfection or sterilization.

The precautions and dangers encountered with the prior art disinfectants and sterilants are greatly reduced by the present invention due to the reduced concentrations. This improvement is made possible by the fact that the disinfecting and sterilant agent glutaraldehyde is enhanced by the synergistic action of the two phenols (orthophenyl phenol and paratertiaryamyl phenol) which are interactive and additive, making the sum greater than any of the parts.

As can be readily understood from the foregoing description of the invention, the present structured formulation of a chemical disinfectant and sterilant can be further structured in different modes of formulation to provide an ability to disinfect and sterilize objects.

Accordingly, modifications and variations to which the invention is susceptible may be practiced without departing from the scope and intent of the appended claims.

What is claimed is:

1. A chemical disinfectant and sterilant, comprising: a basic formulation of chemical ingredients, said basic formulation of said chemical ingredients consisting of the following optimal quantities of said chemical ingredients, said optimal quantities being by weight of the total weight of said basic formulation: glutaraldehyde (acidic) 227.2 grams; orthophenyl phenol 5.0 grams; paratertiaryamyl phenol 1.0 grams; brenzotriazole 3.5 grams; sodium arylalkylsulfonate 50.0 grams; citric acid 5.0 grams; and 1177.6 grams of water, the total mixture of said disinfectant and sterilant having a total optimal weight of 1469.3 grams, said respective weights of said chemical ingredients and said water being 15.46% glutaraldehyde (acidic), 0.34% orthophenyl phenol, 0.07% paratertiaryamyl phenol, 0.24% benzotriazole, 3.40% sodium arylalkylsulfonate, 0.34% citric acid, and 80.15% water, said formulation of said chemical ingredients forming a base stock solution.

2. A chemical disinfectant and sterilant as recited in claim 1, wherein said chemical ingredients, including said principal chemical ingredient, are liquids.

3. A chemical disinfectant and sterilant as recited in claim 1, wherein said chemical ingredients, including said principal chemical ingredient, are dry ingredients in a powder-like consistency, said dry ingredients being suitably dissolved when being readied for use.

4. A chemical disinfectant and sterilant as recited in claim 1, wherein said glutaraldehyde, being acidic, has a pH range held within 3.0 to 3.5.

5. A chemical disinfectant and sterilant as recited in claim 1, wherein said glutaraldehyde, being acidic, has a pH range of 2.5 to 7.0.

6. A chemical disinfectant and sterilant as recited in claim 1, wherein said glutaraldehyde, being acidic, has a pH range not exceeding 7.0.

7. A chemical disinfectant and sterilant as recited in claim 1 and additionally, ultrasonic activation of the mass, said ultrasonic activation speeding up the process of disinfection.

* * * * *